United States Patent [19]

Morikawa et al.

[11] Patent Number: 5,334,782
[45] Date of Patent: Aug. 2, 1994

[54] METHOD FOR PRODUCING A HYDROGEN-CONTAINING CHLOROMETHANE

[75] Inventors: Shinsuke Morikawa; Masaru Yoshitake; Shin Tatematsu, all of Yokohama, Japan

[73] Assignee: AG Technology Co., Ltd., Yokohama, Japan

[21] Appl. No.: 960,423

[22] PCT Filed: Apr. 23, 1991

[86] PCT No.: PCT/JP92/00522

§ 371 Date: Dec. 23, 1992

§ 102(e) Date: Dec. 23, 1992

[87] PCT Pub. No.: WO92/18447

PCT Pub. Date: Oct. 29, 1992

[30] Foreign Application Priority Data

Apr. 23, 1991 [JP] Japan .................................. 2-119457
Dec. 13, 1991 [JP] Japan .................................. 2-352257

[51] Int. Cl.$^5$ ...................... C07C 17/24; C07C 19/02; C07C 19/04
[52] U.S. Cl. .................................. 570/101; 570/257
[58] Field of Search .......................................... 570/101

[56] References Cited

U.S. PATENT DOCUMENTS

| | | | |
|---|---|---|---|
| 3,579,596 | 5/1971 | Mullin et al. | 570/101 |
| 5,097,081 | 3/1992 | Correia et al. | |
| 5,105,032 | 4/1992 | Holbrook et al. | |
| 5,146,013 | 9/1992 | Dogimont et al. | 570/101 |
| 5,208,393 | 5/1993 | Miguel et al. | 570/101 |

FOREIGN PATENT DOCUMENTS

| | | |
|---|---|---|
| 0479116 | 4/1992 | European Pat. Off. . |
| 2-1414 | 1/1990 | Japan . |
| 3-133939 | 6/1991 | Japan . |
| 4-26636 | 1/1992 | Japan . |
| 91/09827 | 7/1991 | World Int. Prop. O. . |

*Primary Examiner*—Joseph E. Evans
*Attorney, Agent, or Firm*—Oblon, Spivak, McClelland, Maier & Neustadt

[57] ABSTRACT

The present invention relates to a method for producing a hydrogen-containing chloromethane such as chloroform at high selectivity in good yield by reducing a polychloromethane such as carbon tetrachloride in the presence of a reduction catalyst.

In the present invention, it is important to conduct the reduction reaction in a liquid phase, whereby formation of impurities such as polymers which deactivate the catalyst, can effectively be suppressed, and the high selectivity and high activity of the reduction catalyst can adequately be obtained.

As the reduction catalyst, at least one member selected from elements of Groups 8, 9 and 10, such as ruthenium, rhodium, palladium and platinum, may suitably be employed. Also a catalyst comprising, as the main component, such an element and having at least one member of Group 11 elements such as copper, silver and gold added thereto, may also suitably be employed.

In a case where the liquid phase reduction reaction is conducted continuously, it is preferred to adopt a fixed bed system, particularly a trickle bed system.

The method of the present invention is valuable also as a method for converting carbon tetrachloride which is regulated from the standpoint of global environmental protection, to chloroform which is useful as raw material for various fluorine-containing compounds.

6 Claims, No Drawings

METHOD FOR PRODUCING A HYDROGEN-CONTAINING CHLOROMETHANE

DESCRIPTION

1. Technical Field

The present invention relates to a method wherein a polychloromethane, particularly carbon tetrachloride, which is regulated from the standpoint of global environmental protection, is used as a starting material, and this starting material is converted to a hydrogen-containing chloromethane such as chloroform which is useful as a starting material for various fluorine-containing compounds.

2. Background Technique

Heretofore, carbon tetrachloride has been used primarily as a starting material for various chlorofluorocarbons. However, these chlorofluorocarbons as well as carbon tetrachloride as the starting material have been restricted in their production, and a technique to decompose these materials or to convert them to useful materials, has been desired widely throughout the world.

On the other hand, a hydrogen-containing chloromethane such as chloroform obtainable by substituting hydrogen atoms for the chlorine atoms in carbon tetrachloride, is useful as a starting material for various chemical products. Accordingly, it is urgently desired to develop a technique for introducing hydrogen effectively to a polychloromethane such as carbon tetrachloride to convert it to a hydrogen-containing chloromethane.

Various methods have been known to introduce hydrogen to carbon tetrachloride. A method for the electrolytic reduction in the presence of a protic solvent has a drawback such that the reaction is slow, and can hardly be adopted on an industrial basis. On the other hand, a method for the hydrogenation reduction by means of a reduction catalyst as shown, for example, in Japanese Unexamined Patent Publication No. 133939/1991 is believed to be advantageous for development on an industrial basis, since the reaction rate is high, and hydrogen chloride as a by-product can also be utilized. However, the method disclosed in Japanese Unexamined Patent Publication No. 133939/1991 is a gas phase hydrogenation reduction method employing a widely used catalyst such as iron or platinum, whereby it has been found that the catalytic activities decrease in a short period of time. Further, a method of gas phase hydrogenation reduction of carbon tetrachloride has had a problem that the yield of the desired product is not high enough, since a dimmer such as hexachloroethane or a polymer having from 5 to 7 carbon atoms, particularly at a high temperature, tends to form as a by-product.

The present inventors have conducted various studies with respect to the above gas phase hydrogenation reduction method. Firstly, as a result of an analysis of the organic components deposited on a deactivated catalyst, many of them were found to be polymers. Further, from the inspection by a transmission electron microscope and the analysis by the X-ray diffraction, the particle size of the catalyst was found to be substantially the same as the size before use. Therefore, deposition of the polymers is considered to be the primary cause for the deactivation.

DISCLOSURE OF THE INVENTION

The present inventors have conducted an extensive study with respect to a reaction method for controlling the rapid deactivation of the catalyst. As a result, it has been found that the rapid deterioration of the catalyst can be eliminated, and a hydrogen-containing chloromethane can be obtained in good yield by adopting a method which comprises reducing a polychloromethane by hydrogen in a liquid phase state in the presence of a reduction catalyst. The present invention has been accomplished on the basis of this discovery and presents a method for producing a hydrogen-containing chloromethane, which comprises reducing a polychloromethane by hydrogen in a liquid phase in the presence of a reduction catalyst. The present invention will be described in detail hereinafter together with Examples.

The polychloromethane may be carbon tetrachloride, chloroform or methylene chloride. According to the method of the present invention, chloroform, methylene chloride or methyl chloride can be obtained by the reduction of carbon tetrachloride, or methylene chloride or methyl chloride can be obtained by the reduction of chloroform, or methyl chloride can be obtained by the reduction of methylene chloride. The polychloromethane is preferably carbon tetrachloride which is regulated for its use.

Carbon tetrachloride is a molecule having four chlorine atoms with high polarity bonded to a carbon atom, and it has a very large adsorption energy among halogenated methanes. Accordingly, its retention time on the catalyst is long, and it is susceptible to the catalytic activities. Accordingly, when a catalyst comprising an element having high reducing activities selected from Groups 8, 9 and 10, is used, formation of olefins and formation of polymers tend to be remarkable, whereby the catalyst tends to be deactivated in an extremely short period of time. Especially in the gas phase reaction, formation and polymerization of olefins tend to occur, since the reaction temperature is basically high, and the formed polymers tend to be hardly removed from the catalyst surface, since such polymers usually have high boiling points. This is believed to be a cause for the rapid deactivation.

On the other hand, to conduct the reaction in a liquid phase, the reaction system is likely to be complicated. However, some merits are conceivable such that adsorption of carbon tetrachloride can easily be controlled, for example, by using a solvent for the reaction, and by-product polymers can easily be dissolved and removed from the catalyst surface if their degrees of polymerization are not high, whereby it may be possible to control the decrease of active sites. Under these circumstances, a study has been made to optimize the reaction conditions and the catalyst. As a result, it has been found that a hydrogen-containing chloromethane such as chloroform, methylene chloride or methyl chloride can be obtained at high selectively without rapid deactivation of the catalyst.

As the reduction catalyst, a catalyst comprising, as the main component, at least one element selected from Group 8 elements such as iron, ruthenium and osmium, Group 9 elements such as cobalt, rhodium and iridium and Group 10 elements such as nickel, palladium and platinum, is preferred. Such a catalyst comprising, as the main component, a Group 8, 9 or 10 element, may be a catalyst composed solely of such an element or a catalyst which may have a metal element other than the Group 8 to 10 elements further added to and used in combination with such an element.

Among the Group 8 to 10 elements as the main component, a platinum group element such as palladium, ruthenium, platinum or rhodium is particularly preferred, since high activities and high durability can easily be obtained. Further, as additional components, Group 11 elements such as copper, silver and gold, may, for example, be mentioned. Both the main component elements and the additional component elements may be used alone or in combination as a mixture of two or more. When the additional component is used in combination, its amount is usually from 0.01 to 50% by weight, preferably from 0.1 to 50% by weight, more preferably from 1 to 50% by weight.

Such a catalyst metal may be used as it is or as supported on a carrier. As the carrier, a commonly employed carrier such as active carbon, alumina, zirconia or silica, may be employed. The amount to be supported is usually from 0.01 to 20% by weight, preferably from 0.5 to 5% by weight, from the viewpoint of the supporting efficiency of the catalyst, the activities for reaction and the dispersion of the catalyst component.

The supporting method of the catalyst component may also be optionally selected within the conventional range. For example, it is possible to employ a dipping method or an ion exchange method using a simple salt or a complex salt of the above element. Further, when the catalyst is to be used, it is not always necessary to conduct reduction treatment of the catalyst, but it is preferred to preliminarily apply hydrogenation reduction to obtain constant properties. As a method for reducing a supported catalyst component, it is possible to employ a method of reducing in a liquid phase by e.g. hydrogen, hydrazine, formaldehyde or sodium boron hydride, or a method of reducing in a gas phase by hydrogen.

Either a fixed bed system or a suspension bed system may be employed for the liquid phase reaction process. It is effective to use a solvent for reaction to control the proportions of the products or to stabilize the activities for reaction, and a solvent may optionally be used. For example, an alcohol such as methanol or ethanol, an amine such as triethylamine, a carboxylic acid such as acetic acid or a ketone such as acetone, can be used as the solvent for reaction.

To conduct the liquid phase reduction reaction of the present invention continuously, it is advisable to adopt a liquid phase fixed bed system wherein the starting material solution is contacted to a fixed bed of the reduction catalyst. Especially, in a trickle bed system wherein the starting material liquid is supplied in a downflow fashion, the liquid phase diffusion distance of hydrogen is short, and the decrease of the hydrogen concentration on the catalyst surface can easily be controlled. Accordingly, such a trickle bed system is advantageous for improving the reaction rate and the catalyst durability. In the liquid phase fixed bed system, it is advisable to use a catalyst having a catalyst metal supported on a carrier. As the carrier, it is advisable to use the one having a strength at a level such that it will not undergo pulverization by the flow of the liquid. The shape of the carrier is preferably a pellet which is hardly damaged by abrasion, in a case where the starting material liquid is supplied in an upflow fashion. However, in the trickle bed system, pulverized carbon may also be used, and the shape is not particularly limited. Also with respect to the size of the catalyst, there is no particular restriction, but the diameter is usually preferably from about 0.5 to about 20 mm.

The temperature for the liquid phase reduction reaction is usually from 0° C. to 200° C., preferably from 50° C. to 150° C. There is no particular restriction as to the molar ratio for reaction of hydrogen to the polychloromethane. If hydrogen is increased, the reaction rate increases, but the proportion of the products having dechlorination and hydrogenation more advanced increases. It is preferred to use hydrogen in an amount of from about 0.1 to 10 mols per mol of the polychloromethane. Excess hydrogen may be recycled, whereby the utilization efficiency of hydrogen can be increased.

Further, the reaction pressure is usually at least atmospheric pressure. As the pressure is raised, the reaction rate increases. An elevated pressure of from a few $kg/cm^2G$ too 10 $kg/cm^2G$ may be employed. If the pressure is too high, there will be a drawback that the cost for the apparatus increases, although the reaction rate can be increased.

BEST MODE FOR CARRYING OUT THE INVENTION

Now, Examples of the present invention will be described. EXAMPLE 1

Into an autoclave having an internal capacity of 2ℓ, 1ℓ of carbon tetrachloride was introduced, and a platinum catalyst supported on active carbon (supported amount: 2% by weight, manufactured by N E Chemcat Company) was added in an amount of 10 g. Nitrogen was sealed in, and the temperature was raised to 110° C. Then, supply of hydrogen was initiated. The pressure was 5 $kg/cm^2G$. The products were analyzed by gas chromatography with respect to each of the gas phase components and the liquid phase components. The reaction was continued by continuously supplying 3 mols of hydrogen per mol of carbon tetrachloride. The reaction rate of carbon tetrachloride upon expiration of 1,000 hours after the initiation of the reaction, was 91%, and formation of chloroform (selectivity: 70%), perchloroethylene (selectivity: 18%), etc. was confirmed.

EXAMPLE 2

Into an autoclave having an internal capacity of 2ℓ, 1ℓ of carbon tetrachloride was introduced, and a palladium catalyst supported on alumina (supported amount: 2% by weight, manufactured by N E Chemcat Company) was added in an amount of 50 g. Nitrogen was sealed in, and then the temperature was raised to 115° C. Then, supply of hydrogen was initiated. The pressure was 5 $kg/cm^2G$. The products were analyzed by gas chromatography with respect to each of the gas phase components and the liquid phase components. The reaction was continued by continuously supplying 4 mols of hydrogen per mol of carbon tetrachloride. The reaction rate of carbon tetrachloride upon expiration of 1,000 hours after the initiation of the reaction, was 92%, and formation of chloroform (selectivity: 60%), methylene chloride (selectivity: 9%), perchloroethylene (selectivity: 17%), etc. was confirmed.

EXAMPLE 3

Into an autoclave having an internal capacity of 2ℓ, 1ℓ of carbon tetrachloride was introduced, and a rhodium catalyst supported on zirconia (supported amount: 2% by weight, manufactured by N E Chemcat Company) was added in an amount of 50 g. Nitrogen was sealed in, and the temperature was raised to 110° C. Then, supply of hydrogen was initiated. The pressure was 5 kg/cm$^2$G. The products were analyzed by gas chromatography with respect to each of the gas phase components and the liquid phase components. The reaction was continued by continuously supplying 3 mols of hydrogen per mol of carbon tetrachloride. The reaction rate of carbon tetrachloride upon expiration of 1,000 hours after the initiation of the reaction, was 93%, and formation of chloroform (selectivity: 58%), methylene chloride (selectivity: 8%), methyl chloride (selectivity: 7%), perchloroethylene (selectivity: 16%), etc. was confirmed.

EXAMPLE 4

Into an autoclave having an internal capacity of 2$l$, 1$l$ of carbon tetrachloride was introduced, and a ruthenium catalyst supported on active carbon (supported amount: 5% by weight, manufactured by N E Chemcat Company) was added in an amount of 50 g. Nitrogen was sealed in, and the temperature was raised to 120° C. Then, supply of hydrogen was initiated. The pressure was 5 kg/cm$^2$G. The products were analyzed by gas chromatography with respect to each of the gas phase components and the liquid phase components. The reaction was continued by continuously supplying 5 mols of hydrogen per mol of carbon tetrachloride. The reaction rate of carbon tetrachloride upon expiration of 1,000 hours after the initiation of the reaction, was 89%, and formation of chloroform (selectivity: 58%), methylene chloride (selectivity: 9%), methyl chloride (selectivity: 14%), perchloroethylene (selectivity: 18%), etc. was confirmed.

COMPARATIVE EXAMPLE 1

100 g of a platinum catalyst supported on active carbon (supported amount: 0.5% by weight, manufactured by N E Chemcat Company) was introduced into an Inconel reaction tube having an inner diameter of 1.5 inch, and immersed in a heat medium set at 160° C. It was preliminarily treated with nitrogen and then with hydrogen. Then, a reaction was conducted in a gas phase by introducing hydrogen at a rate of 2 mols per mol of carbon tetrachloride. The contact time was 7 seconds, and the reaction pressure was atmospheric pressure. The reaction rates of carbon tetrachloride upon expiration of two hours and 20 hours after initiation of the reaction were about 90% and about 30%, respectively, and thereafter, the catalyst was deactivated with time. As the products, chlorinated alkanes and alkenes having from 2 to 5 carbon atoms, such as perchloroethylene, were observed in addition to chloroform, methylene chloride, methyl chloride and methane.

EXAMPLE 5

4$l$ of a platinum catalyst supported on molded carbon having a diameter of 3 mm (supported amount: 2% by weight, manufactured by N E Chemcat Company) was packed into a cylindrical reactor having an inner diameter of 60 mm. The catalyst layer was filled with carbon tetrachloride and then nitrogen was sealed in. The temperature was raised to 80° C., and then supply of hydrogen was initiated. The reaction was continued by continuously supplying 3 mols of hydrogen per mol of carbon tetrachloride in an upflow fashion. The formed gas components such as chloroform were continuously taken out by a gas-liquid separator, and the liquid components such as non-reacted carbon tetrachloride were returned to the reactor for recycling. The pressure was 5 kg/cm$^2$G. The products were analyzed by gas chromatography with respect to each of the gas phase components and the liquid phase components. The reaction rate by one pass of carbon tetrachloride upon expiration of 100 hours after initiation of the reaction, was 91%, and formation of chloroform (selectivity: 90%), perchloroethylene (selectivity: 5%), etc. was confirmed.

EXAMPLE 6

An experiment was conducted in the same manner as in Example 5 except that as a catalyst, a palladium catalyst supported on molded carbon having a diameter of 5 mm (supported amount: 2% by weight, manufactured by N E Chemcat Company) was used, and an analysis of the products was conducted. The reaction rate by one pass of carbon tetrachloride upon expiration of 100 hours after initiation of the reaction, was 92%, and formation of chloroform (selectivity: 85%), perchloroethylene (selectivity: 10%), methane (5%), etc. was confirmed.

EXAMPLE 7

1$l$ of a platinum catalyst supported on molded carbon having a diameter of 1 mm (supported amount: 2% by weight, manufactured by N E Chemcat Company) was packed into a cylindrical reactor having an inner diameter of 30 mm. Nitrogen was filled, and then the temperature was raised to 80° C. The catalyst was thoroughly reduced by hydrogen, and then hydrogen and carbon tetrachloride were supplied in a downflow fashion at a molar ratio of 5:1. The products were analyzed by gas chromatography with respect to each of the gas phase components and the liquid phase components. The reaction rate of carbon tetrachloride upon expiration of 100 hours after initiation of the reaction, was 94%, and formation of chloroform (selectivity: 90%), perchloroethylene (selectivity: 5%), etc. was confirmed.

Now, Examples for preparing reduction catalysts having additional component elements incorporated will be given, and specific Examples for the liquid phase reduction reaction using such reduction catalysts will be given.

PREPARATION EXAMPLE 1

As a carrier, 100 g of coconut-shell active carbon powder (average particle size: 10–20 μm) was put into 1$l$ of deionized water. Ruthenium chloride and chloroauric acid were dissolved in deionized water in an amount corresponding to 5% of the weight of the carrier in such a ratio that the weight ratio of the respective metal components would be 9:1. The catalyst was reduced by an aqueous solution of hydrazine, then washed with deionized water and dried at 110° C.

PREPARATION EXAMPLE 2

As a carrier, 100 g of acetylene black powder (average particle size: 1 μm) was put into 1$l$ of deionized water. Rhodium chloride and chloroauric acid were dissolved in deionized water in an amount corresponding to 2% of the weight of the carrier in such a ratio that the weight ratio of the respective metal components would be 95:5. The catalyst was reduced by an aqueous solution of sodium boron hydride, then washed with deionized water and dried at 110° C.

PREPARATION EXAMPLE 3

As a carrier, 100 g of pitch-type active carbon powder (average particle size: 10-20 μm) was put into 1ℓ of deionized water. Palladium chloride and chloroauric acid were dissolved in deionized water in an amount corresponding to 2% of the weight of the carrier in such a ratio that the weight ratio of the respective metal components would be 8:2. The catalyst was reduced by an aqueous solution of hydrazine, then washed with deionized water and dried at 110° C.

PREPARATION EXAMPLE 4

As a carrier, 100 g of pitch-type active carbon powder (average particle size: 10-20 μm) was put into 1ℓ of deionized water. Nickel chloride, chloroplatinic acid and chloroauric acid were dissolved in deionized water in an amount corresponding to 2% of the weight of the carrier in such a ratio that the weight ratio of the respective metal components would be 5:4:1. The catalyst was reduced by an aqueous solution of sodium boron hydride, then washed with deionized water and dried at 110° C.

PREPARATION EXAMPLE 5

As a carrier, 100 g of wood-type active carbon powder (average particle size: 10-20 μm) was put into 1ℓ of deionized water. Chloroplatinic acid and chloroauric acid were dissolved in deionized water in an amount corresponding to 2% of the weight of the carrier in such a ratio that the weight ratio of the respective metal components would be 9:1. The catalyst was reduced by an aqueous solution of sodium boron hydride, then washed with deionized water and dried at 110° C.

PREPARATION EXAMPLE 6

As a carrier, 100 g of coconut-shell active carbon powder (average particle size: 10-20 μm) was put into 1ℓ of deionized water. Ruthenium chloride and diamine silver nitrate were dissolved in deionized water in an amount corresponding to 5% of the weight of the carrier in such a ratio that the weight ratio of the respective metal components would be 85:15. The solution was alkalized by an addition of aqueous ammonia. Then, the catalyst was reduced by an aqueous solution of sodium boron hydride, then washed with deionized water and dried at 110° C.

PREPARATION EXAMPLE 7

As a carrier, 100 g of coconut-shell active carbon powder (average particle size: 10-20 μm) was put into 1ℓ of deionized water. Rhodium chloride and diamine silver nitrate were dissolved in deionized water in an amount corresponding to 2% of the weight of the carrier in such a ratio that the weight ratio of the respective metal components would be 9:1. The catalyst was reduced by an aqueous solution of hydrazine, then washed with deionized water and dried at 110° C.

PREPARATION EXAMPLE 8

As a carrier, 100 g of pitch-type active carbon powder (average particle size: 10-20 μm) was put into 1ℓ of deionized water. Palladium chloride and diamine silver were dissolved in deionized water in an amount corresponding to 2% of the weight of the carrier in such a ratio that the weight ratio of the respective metal components would be 95:5. The solution was alkalized by an addition of aqueous ammonia. Then, the catalyst was reduced by an aqueous solution of hydrazine, then washed with deionized water and dried at 110° C.

PREPARATION EXAMPLE 9

As a carrier, 100 g of coconut-shell active carbon powder (average particle size: 10-20 μm) was put into 1ℓ of deionized water. Chloroplatinic acid and diamine silver were dissolved in deionized water in an amount corresponding to 2% of the weight of the carrier in such a ratio that the weight ratio of the respective metal components would be 9:1. The solution was alkalized by an addition of aqueous ammonia. Then, the catalyst was reduced by an aqueous solution of hydrazine, then washed with deionized water and dried at 110° C.

PREPARATION EXAMPLE 10

As a carrier, 100 g of coconut-shell active carbon powder (average particle size: 10-20 μm) was put into 1ℓ of deionized water. Ruthenium chloride and copper chloride were dissolved in deionized water in an amount corresponding to 5% of the weight of the carrier in such a ratio that the weight ratio of the respective metal components would be 95:5. The solution was alkalized by an addition of aqueous ammonia. Then, the catalyst was reduced by an aqueous solution of sodium boron hydride, then washed with deionized water and dried at 110° C.

PREPARATION EXAMPLE 11

As a carrier, 100 g of wood-type active carbon powder (average particle size: 10-20 μm) was put into 1ℓ of deionized water. Rhodium chloride and copper chloride were dissolved in deionized water in an amount corresponding to 2% of the weight of the carrier in such a ratio that the weight ratio of the respective metal components would be 9:1. The solution was alkalized by an addition of aqueous ammonia. Then, the catalyst was reduced by an aqueous solution of hydrazine, then washed with deionized water and dried at 110° C.

PREPARATION EXAMPLE 12

As a carrier, 100 g of pitch-type active carbon powder (average particle size: 10-20 μm) was put into 1ℓ of deionized water. Palladium chloride and copper chloride were dissolved in deionized water in an amount corresponding to 2% of the weight of the carrier in such a ratio that the weight ratio of the respective metal components would be 95:5. The solution was alkalized by an addition of aqueous ammonia. Then, the catalyst was reduced by an aqueous solution of hydrazine, then washed with deionized water and dried at 110° C.

PREPARATION EXAMPLE 13

As a carrier, 100 g of coconut-shell active carbon powder (average particle size: 10-20 μm) was put into 1ℓ of deionized water. Chloroplatinic acid and copper chloride were dissolved in deionized water in an amount corresponding to 2% of the weight of the carrier in such a ratio that the weight ratio of the respective metal components would be 9:1. The solution was alkalized by an addition of aqueous ammonia. Then, the catalyst was reduced by an aqueous solution of hydrazine, then washed with deionized water and dried at 110° C.

EXAMPLE 8

Into an autoclave having an internal capacity of 2ℓ, 1ℓ of carbon tetrachloride was introduced, and 50 g of the reduction catalyst prepared in Preparation Example 1 was added. Nitrogen was sealed in, and the temperature was raised to 80° C. Then, supply of hydrogen was initiated. The pressure was maintained at 5 kg/cm$^2$G. The products were analyzed by gas chromatography with respect to each of the gas phase components and the liquid phase components. The reaction was continued by continuously supplying hydrogen at a rate of 3 mols per mol of carbon tetrachloride. The reaction rate of carbon tetrachloride upon expiration of 100 hours after initiation of the reaction, was 86%, and formation of chloroform (selectivity: 95%), hexachloroethane (selectivity: 5%), etc. was confirmed.

EXAMPLE 9

The reaction was conducted in the same manner as in Example 8 except that the reduction catalyst prepared in Preparation Example 2 was used, and the reaction temperature was changed to 110° C. The reaction rate of carbon tetrachloride upon expiration of 100 hours after initiation of the reaction, was 78%, and formation of chloroform (selectivity: 85%), hexachloroethane (selectivity: 5%), methylene chloride (selectivity: 8%), etc. was confirmed.

EXAMPLE 10

The reaction was conducted in the same manner as in Example 8 except that the reduction catalyst prepared in Preparation Example 3 was used, and the reaction temperature was changed to 100° C. The reaction rate of carbon tetrachloride upon expiration of 100 hours after initiation of the reaction, was 85%, and formation of chloroform (selectivity: 90%), hexachloroethane (selectivity: 5%), pentachloroethane (selectivity: 2%), tetrachloroethylene (selectivity: 2%), etc. was confirmed.

EXAMPLE 11

The reaction was conducted in the same manner as in Example 8 except that the reduction catalyst prepared in Preparation Example 4 was used. The reaction rate of carbon tetrachloride upon expiration of 100 hours after initiation of the reaction, was 86%, and formation of chloroform (selectivity: 92%), hexachloroethane (selectivity: 4%), etc. was confirmed.

EXAMPLE 12

The reaction was conducted in the same manner as in Example 8 except that the reduction catalyst prepared in Preparation Example 5 was used, and the reaction temperature was changed to 100° C. The reaction rate of carbon tetrachloride upon expiration of 100 hours after initiation of the reaction, was 84%, and formation of chloroform (selectivity: 89%), hexachloroethane (selectivity: 6%), etc. was confirmed.

EXAMPLE 13

The reaction was conducted in the same manner as in Example 8 except that the reduction catalyst prepared in Preparation Example 6 was used. The reaction rate of carbon tetrachloride upon expiration of 100 hours after initiation of the reaction, was 90%, and formation of chloroform (selectivity: 92%), hexachloroethane (selectivity: 3%), etc. was confirmed.

EXAMPLE 14

The reaction was conducted in the same manner as in Example 8 except that the reduction catalyst prepared in Preparation Example 7 was used, and the reaction temperature was changed to 110° C. The reaction rate of carbon tetrachloride upon expiration of 100 hours after initiation of the reaction, was 75%, and formation of chloroform (selectivity: 85%), hexachloroethane (selectivity: 6%), methylene chloride (selectivity: 7%), etc. was confirmed.

EXAMPLE 15

The reaction was conducted in the same manner as in Example 8 except that the reduction catalyst prepared in Preparation Example 8 was used, and the reaction temperature was changed to 100° C. The reaction rate of carbon tetrachloride upon expiration of 100 hours after initiation of the reaction, was 71%, and formation of chloroform (selectivity: 90%), hexachloroethane (selectivity: 4%), pentachloroethane (selectivity: 2%), tetrachloroethylene (selectivity: 2%), etc. was confirmed.

EXAMPLE 16

The reaction was conducted in the same manner as in Example 8 except that the reduction catalyst prepared in Preparation Example 9 was used. The reaction rate of carbon tetrachloride upon expiration of 100 hours after initiation of the reaction, was 84%, and formation of chloroform (selectivity: 97%), tetrachloroethane (selectivity: 3%), etc. was confirmed.

EXAMPLE 17

The reaction was conducted in the same manner as in Example 8 except that the reduction catalyst prepared in Preparation Example 10 was used. The reaction rate of carbon tetrachloride upon expiration of 100 hours after initiation of the reaction, was 83%, and formation of chloroform (selectivity: 69%), hexachloroethane (selectivity: 28%), methylene chloride (selectivity: 1%), tetrachloroethylene (selectivity: 2%), etc. was confirmed.

EXAMPLE 18

The reaction was conducted in the same manner as in Example 8 except that the reduction catalyst prepared in Preparation Example 11 was used, and the reaction temperature was changed to 120° C. The reaction rate of carbon tetrachloride upon expiration of 100 hours after initiation of the reaction, was 84%, and formation of chloroform (selectivity: 87%), hexachloroethane (selectivity: 6%), methylene chloride (selectivity: 7%), etc. was confirmed.

EXAMPLE 19

The reaction was conducted in the same manner as in Example 8 except that the reduction catalyst prepared in Preparation Example 12 was used, and the reaction temperature was changed to 90° C. The conversion rate of carbon tetrachloride upon expiration of 100 hours after initiation of the reaction, was 74%, and formation of chloroform (selectivity: 89%), hexachloroethane (selectivity: 5%), pentachloroethane (selectivity: 2%), tetrachloroethylene (selectivity: 3%), etc. was confirmed.

EXAMPLE 20

The reaction was conducted in the same manner as in Example 8 except that the reduction catalyst prepared in Preparation Example 13 was used. The conversion of carbon tetrachloride upon expiration of 100 hours after initiation of the reaction, was 87%, and formation of chloroform (selectivity: 93%), hexachloroethane (selectivity: 5%), etc. was confirmed.

As shown by the Examples, the present invention has an effect such that a hydrogen-containing chloromethane such as chloroform can be produced in good yield by reducing a polychloromethane, particularly carbon tetrachloride, in a liquid phase by means of hydrogen. Further, the method of the present invention has an effect such that even when the conversion of the starting material polychloromethane is increased, the desired hydrogen-containing chloromethane such as chloroform can be obtained at high selectivity. Furthermore, in the method of the present invention, a side reaction for forming impurities which impair the catalytic activities, can effectively be controlled. Therefore, the method is very advantageous also from the viewpoint of the useful life of the catalyst.

We claim:

1. A method for producing a hydrogen-containing chloromethane, which comprises reducing a polychloromethane by hydrogen in a liquid phase fixed bed system in the presence of a reduction catalyst, wherein said reduction catalyst comprises:
   (A) at least one element selected from the group consisting of ruthenium, rhodium, palladium and platinum, or
   (B) as the main component at least one element selected from the group consisting of ruthenium, rhodium, palladium and platinum, and at least one additional component element selected from the group consisting of copper, silver and gold.

2. The method according to claim 1, wherein the amount of the additional component element in the reduction catalyst is from 0.01 to 50% by weight.

3. The method according to claim 1, wherein the reduction temperature is from 0° C. to 200° C.

4. The method according to claim 1, wherein the polychloromethane is carbon tetrachloride.

5. The method according to claim 1, wherein said reduction catalyst comprises (A).

6. The method according to claim 1, wherein said reduction catalyst comprises (B).

* * * * *

UNITED STATES PATENT AND TRADEMARK OFFICE
CERTIFICATE OF CORRECTION

PATENT NO. : 5,334,782
DATED      : August 2, 1994
INVENTOR(S): Shinsuke MORIKAWA, et al.

It is certified that error appears in the above-indentified patent and that said Letters Patent is hereby corrected as shown below:

On the Title Page, Item [22], the PCT filing date should read:
--Apr. 23, 1992--

On the Title Page, Item [30], the Foreign Application Priority Numbers should read:

--3-119457-- and --3-352257--

Signed and Sealed this

Fifteenth Day of November, 1994

Attest:

BRUCE LEHMAN

*Attesting Officer*      *Commissioner of Patents and Trademarks*